US012704515B2

(12) United States Patent
Cotham et al.

(10) Patent No.: US 12,704,515 B2
(45) Date of Patent: Aug. 11, 2026

(54) ONLINE NATIVE MASS SPECTROMETRY METHODS FOR ASSAYING VIRAL PARTICLES

(71) Applicant: Regeneron Pharmaceuticals, Inc., Tarrytown, NY (US)

(72) Inventors: Victoria Cotham, Lagrangeville, NY (US); Shunhai Wang, Scarsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1035 days.

(21) Appl. No.: 17/862,248

(22) Filed: Jul. 11, 2022

(65) Prior Publication Data

US 2023/0010418 A1 Jan. 12, 2023

Related U.S. Application Data

(60) Provisional application No. 63/352,754, filed on Jun. 16, 2022, provisional application No. 63/220,654, filed on Jul. 12, 2021.

(51) Int. Cl.

| | |
|---|---|
| ***G01N 33/00*** | (2006.01) |
| ***B01D 15/16*** | (2006.01) |
| ***B01D 15/36*** | (2006.01) |
| ***C12N 7/00*** | (2006.01) |
| ***G01N 30/72*** | (2006.01) |
| ***G01N 33/569*** | (2006.01) |

(52) U.S. Cl.

CPC ..... *G01N 33/56983* (2013.01); *B01D 15/166* (2013.01); *B01D 15/363* (2013.01); *C12N 7/00* (2013.01); *G01N 30/7233* (2013.01); *C12N 2750/14123* (2013.01); *C12N 2750/14151* (2013.01)

(58) Field of Classification Search

CPC .............................................. G01N 33/56983
USPC ......................................................... 436/173
See application file for complete search history.

(56) References Cited

U.S. PATENT DOCUMENTS

2021/0009964 A1 1/2021 Khatwani et al.
2021/0041451 A1 2/2021 Jin et al.
2023/0204595 A1 6/2023 Daud et al.

FOREIGN PATENT DOCUMENTS

WO 2007/024715 A2 3/2007
WO 2020/056077 A1 3/2020
WO 21/138381 A1 7/2021

OTHER PUBLICATIONS

U.S. Appl. No. 63/220,651, filed Jul. 12, 2021, Expired.
U.S. Appl. No. 63/275,138, filed Nov. 3, 2021, Expired.
U.S. Appl. No. 63/359,554, filed Jul. 8, 2022, Pending.
U.S. Appl. No. 17/862,240, filed Jul. 11, 2022, US-2023-0016717-A1, Published.
PCT/US2022/036723, Jul. 11, 2022, WO 2023/287723, Published.
U.S. Appl. No. 63/220,654, filed Jul. 12, 2021, Expired.

(Continued)

*Primary Examiner* — Lyle Alexander
*Assistant Examiner* — Emily R. Berkeley
(74) *Attorney, Agent, or Firm* — Schwabe, Williamson & Wyatt PC; Angela Guo

(57) ABSTRACT

Methods for determining the relative abundance of viral capsid components in a sample of viral particles are disclosed. In embodiments, methods for determining the relative abundance of empty capsids, partially-full capsids and full capsids (e.g., containing a heterologous nucleic acid molecule) of adeno-associated virus are disclosed.

20 Claims, 10 Drawing Sheets

(56) References Cited

OTHER PUBLICATIONS

U.S. Appl. No. 63/352,754, filed Jun. 16, 2022, Pending.
PCT/US2022/036725, Jul. 11, 2022, WO 2023/287724, Published.
U.S. Appl. No. 63/359,557, filed Jul. 8, 2022, Pending.
U.S. Appl. No. 17/862,254, filed Jul. 11, 2022, US-2023-0020428-A1, Published.
PCT/US2022/036728, Jul. 11, 2022, WO2023/287725, Published.
Liu et al., "Characterization of Adeno-Associated Virus Capsid Proteins Using Hydrophilic Interaction Chromatography Coupled with Mass Spectrometry," Journal of Pharmaceutical and Biomedical Analysis, vol. (189): 1-8, (2020).
Lock et al., "Analysis of Particle Content of Recombinant Adeno-Associated Virus Serotype 8 Vectors by Ion-Exchange Chromatography," Human Gene Therapy Methods, Part B, vol. (23): 56-64, (2012). [DOI: 10.1089/hgtb.2011.217].
Pierson et al., "Resolving Adeno-Associated Viral Particle Diversity With Charge Detection Mass Spectrometry," Analytical Chemistry, American Chemical Society, vol. (88): 6718-6725, (2016).
Qu et al., "Separation of adeno-associated virus type 2 empty particles from genome containing vectors by anion-exchange col. chromatography," ScienceDiet, Journal of Virological Methods, vol. (140): 183-192, (2007).
Wang et al., "Developing an Anion Exchange Chromatography Assay for Determining Empty and Full Capsid Contents in AAV6.2," Methods & Clinical Development, American Society of Gene & Cell Therapy, vol. (15): 257-263, (2019).
WIPO Application No. PCT/US2022/036723, PCT International Search Report and Written Opinion of the International Searching Authority mailed Oct. 18, 2022.
WIPO Application No. PCT/US2022/036728, PCT International Search Report and Written Opinion of the International Searching Authority mailed Oct. 21, 2022.
WIPO Application No. PCT/US2022/036725, PCT International Search Report and Written Opinion of the International Searching Authority mailed Oct. 26, 2022.
Worner et al., "Mass Spectrometry-Based Structural Virology," Analytical Chemistry, American Chemical Society, vol. (93): 620-640, (2021).
Ma et al., "Online Integration of Multiple Sample Pretreatment Steps Involving Denaturation, Reduction, and Digestion with Microflow Reversed-Phase Liquid CHromatography-Electrospray Ionization Tamdem Mass Spectrometry for High-Throughput Proteome Profiling," Analytical Chemoistry, vol. 81 (No. 15): 6534-6540, (2009).
Mahoney et al., "Separation of Large Denatured Peptides by Reverse Phase High Performance Liquid Chromatography," The Journal of Biological Chemistry, vol. 255 (No. 23): 11199-11203, (1980).
Papatheocharidou et al., "Two-Dimensional High-Performance Liquid Chromatography as a Powerful Tool for Bioanalysis: The Paradigm of Antibiotics," Molecules, vol. 28, 5056: pp. 1-17, (2023). [https://doi.org/10.3390/molecules28135056].
U.S. Appl. No. 17/862,254, Non-Final Office Action mailed May 1, 2025.
U.S. Appl. No. 17/862,240, Non-Final Office Action mailed Jul. 10, 2025.
U.S. Appl. No. 17/862,240, Final Office Action mailed Oct. 31, 2025.
U.S. Appl. No. 17/862,254, Notice of Allowance mailed Nov. 4, 2025.
Wang et al, "Developing an Anion Exchange Chromatography Assay for Determining Empty and Full Capsid Contents in AAV6.2", Molecular Therapy: Methods & Clinical Development (2019) vol. 15, pp. 257-263.

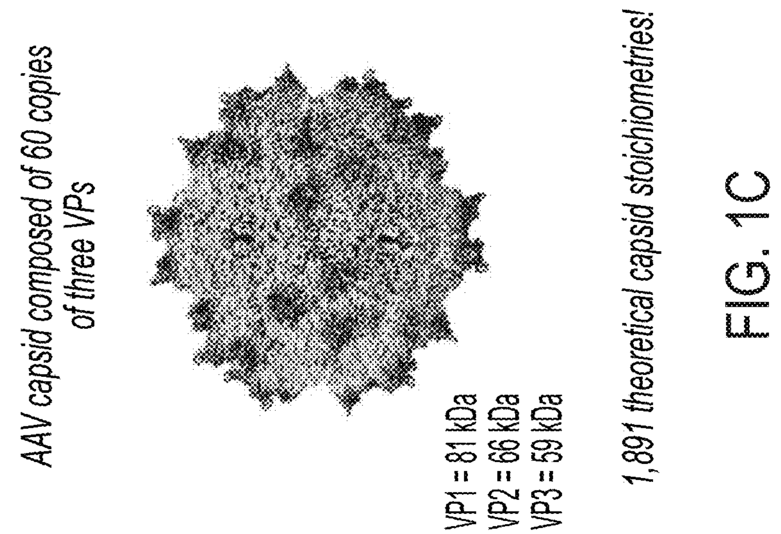
FIG. 1C
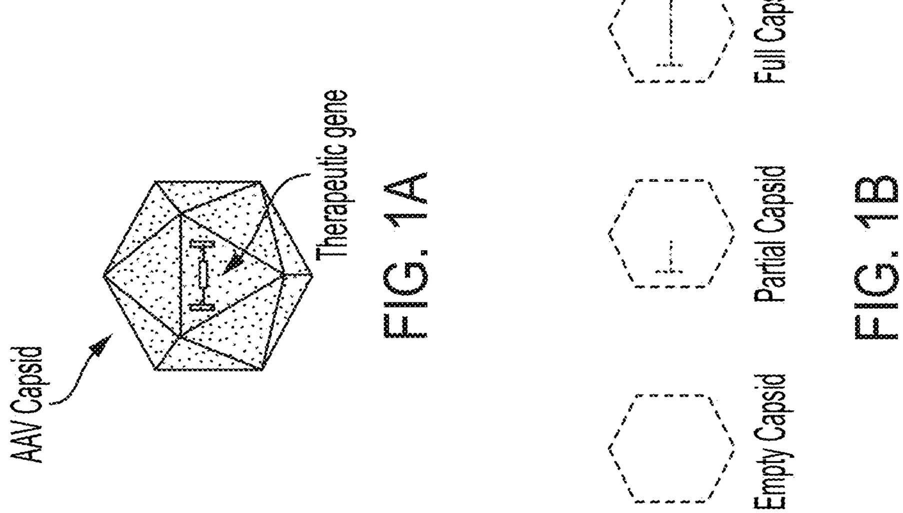
FIG. 1A
FIG. 1B

SV-AUC Capsid Content Quantitation:

| AAV Serotype | Empty | Partial | Full | Titer (capsids/mL) |
|---|---|---|---|---|
| AAV1 | 25% | 35% | 40% | 3.25E+13 |
| AAV5 | 48% | 25% | 27% | 4.61E+13 |
| AAV8 | 14% | 3% | 83% | 1.23E+13 |

AUC Capsid Content Ratio:

| Sample | Empty% | Partial% | Full% |
|---|---|---|---|
| AAV8 Full | 14 | 3 | 83 |
| AAV8 Empty | 100 | 0 | 0 |

ONLINE NATIVE MASS SPECTROMETRY METHODS FOR ASSAYING VIRAL PARTICLES

CROSS-REFERENCE TO RELATED APPLICATIONS

This application claims the benefit under 35 USC § 119(e) of US Provisional Application Nos.: 63/220,654, filed Jul. 12, 2021; and 63/352,754, filed Jun. 16, 2022, each of which is incorporated herein by reference in its entirety for all purposes.

FIELD OF THE INVENTION

The present invention relates to methods for quantitative determination of full, partial, and empty viral capsids (e.g., AAV capsids) using online native mass spectrometry.

BACKGROUND

Adeno-associated viruses (AAVs) represent a leading platform for therapeutic gene delivery, with multiple FDA approved AAV-based therapies currently on the market and more than 250 candidates undergoing clinical trials. The fast-paced development of this class of therapeutics places a high demand on robust analytical methods capable of efficiently monitoring product quality to ensure safety and efficacy, as well as to support manufacturing and process development.

Analytical ultracentrifugation (AUC) is a widely-used method for the quantitative analysis of macromolecules in solution. AUC has broad applications for the study of biomacromolecules in a wide range of solvents and over a wide range of solute concentrations. In sedimentation velocity analytical ultracentrifugation (SV-AUC), the movement of solutes in high centrifugal fields is interpreted using hydrodynamic theory to define the size, shape and interactions of macromolecules. Sedimentation equilibrium is a thermodynamic method where equilibrium concentration gradients at lower centrifugal fields are analyzed to define molecule mass, assembly stoichiometry, association constants and solution nonideality. SV-AUC can be used to determine the homogeneity of a sample and provide a detailed picture of the nature of the species present in solution (Cole et al., *Methods Cell Biol.,* 84:143-179, 2008).

In the context of AAV analysis, SV-AUC is regarded as a state-of-art method, as it provides high resolution and wide applicability for analysis of AAVs of different serotypes (Khasa et al., *Molecular Therapy: Methods and Clinical Development,* 21:585-591, 2021). However, SV-AUC can be time consuming (e.g., on the order of >5 hours), and require sample sizes in the range of 500 μL. Thus, there remains a need for highly sensitive and rapid analytical methods that are amenable to low titer and in-process sample analysis of viral particles.

BRIEF SUMMARY OF THE INVENTION

The present disclosure provides online native mass spectrometry (MS) methods that provide rapid and quantitative assessment of full, partial and empty viral capsids (e.g., AAV capsids). These methods are highly sensitive for capsid detection (LOD≈1 μg/mL) making them amenable to low titer and in-process samples.

In one aspect, the present disclosure provides a method for determining relative abundance of intact viral capsid components in a sample of recombinant viral particles comprising a heterologous nucleic acid molecule, wherein the method comprises: (a) introducing the sample of viral particles into an online native liquid chromatography mass spectrometry (LC-MS) system, wherein the LC-MS system comprises a liquid chromatography column in fluid communication with an electrospray ionization emitter, a mass spectrometer, and a gas inlet port; (b) separating the viral capsid components in the sample of viral particles via the liquid chromatography column; (c) contacting the viral capsid components with a charge reducing agent via the gas inlet port prior to subjecting the viral capsid components to mass spectral analysis; and (d) identifying a raw fractional amount of a viral capsid component in the sample via mass spectral analysis to determine the relative abundance of each of two or more intact viral capsid components in the sample of viral particles.

In some embodiments, the sample of viral particles comprises adeno-associated virus (AAV) particles. In some cases, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some cases, the AAV particles are of serotype AAV1, AAV5 or AAV8.

In some embodiments, the viral capsid components comprise empty viral capsids and full viral capsids. In some embodiments, the viral capsid components further comprise partially-full viral capsids.

In some embodiments, the liquid chromatography column is a size-exclusion chromatography (SEC) column.

In some embodiments, the charge reducing agent is isopropanol or triethylamine. In some cases, the charge reducing agent comprises a combination of isopropanol and triethylamine. In some cases, the viral capsid components are contacted with the charge reducing agent in nitrogen gas (e.g., desolvation gas).

In some embodiments, the electrospray ionization emitter includes eight nozzles. In some embodiments, the mass spectrometer is a charge detection mass spectrometer.

In one aspect, the present disclosure provides a method for determining relative abundance of intact viral capsid components in a sample of recombinant viral particles comprising a heterologous nucleic acid molecule, wherein the method comprises: (a) subjecting the sample of viral particles to online native electrospray ionization mass spectrometry (ESI-MS) to identify a raw fractional amount of a viral capsid component, wherein the sample is subjected to chromatographic separation and a charge reducing agent prior to native ESI-MS; and (b) determining the relative abundance of the intact viral capsid component in the sample of viral particles.

In some embodiments, the viral capsid components include empty viral capsids and full viral capsids. In some embodiments, the viral capsid components further include partially-full viral capsids.

In some embodiments, the sample of viral particles comprises adeno-associated virus (AAV) particles. In some cases, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some cases, the AAV particles are of serotype AAV1, AAV5 or AAV8.

In some embodiments, the chromatographic separation is performed using a size-exclusion chromatography (SEC) column.

In some embodiments, the charge reducing agent is isopropanol or triethylamine. In some cases, the charge reducing agent is a combination of isopropanol and triethylamine.

In any of the methods discussed above or herein, the sample may comprise 1000 ng of viral capsid components. In some cases, the sample comprises 500 ng of viral capsid components. In some cases, the sample comprises 100 ng of viral capsid components. In some cases, the sample comprises 50 ng of viral capsid components. In some cases, the sample comprises 10 ng of viral capsid components. In some cases, the sample comprises about 5 ng of viral capsid components.

In any of the methods discussed above or herein, the concentration of viral capsid components in the sample may be from 1 μg/mL to 200 μg/mL. In some cases, the concentration of viral capsid components in the sample is less than 100 μg/mL. In some cases, the concentration of viral capsid components in the sample is less than 50 μg/mL. In some cases, the concentration of viral capsid components in the sample is less than 10 μg/mL. In some cases, the concentration of viral capsid components in the sample is less than 5 μg/mL. In some cases, the concentration of viral capsid components in the sample is about 1 μg/mL.

In one aspect, the present disclosure provides a method of purifying a composition of viral particles, wherein the method comprises an anion-exchange enrichment step and a determination of a relative abundance of intact viral capsid components in a sample of the composition, wherein the determination of relative abundance of intact viral capsid components comprises a method discussed above or herein.

In one aspect, the present disclosure provides a method of monitoring stability of a sample of viral particles over a period of time, wherein the method comprises an anion-exchange enrichment step and a determination of a relative abundance of intact viral capsid components in the sample of viral particles, wherein the determination of relative abundance of intact viral capsid components comprises a method discussed above or herein, and wherein the relative abundance of intact viral capsid components is determined at an initial time point and again determined at one or more time points following the initial time point.

In some embodiments of the stability monitoring method, a change in the relative abundance of the intact viral capsid components at the one or more time points compared to the relative abundance at the initial time point is indicative of the stability of the sample of viral particles during the period of time. In some cases, the sample of viral particles is stored under specified conditions during the period of time. In some cases, the specified conditions include humidity conditions and/or temperature conditions. In some cases, the specified conditions include (or further include) agitation conditions and/or one or more freeze/thaw cycles.

In some embodiments, the determination of a relative abundance of intact viral capsid components is performed before the anion-exchange enrichment step. In some embodiments, the determination of a relative abundance of intact viral capsid components is performed after the anion-exchange enrichment step. In some embodiments, the determination of a relative abundance of intact viral capsid components is performed before the anion-exchange enrichment step and after the anion-exchange enrichment step. In some cases, the anion-exchange enrichment step is performed using an anion-exchange chromatography column.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIGS. 1A, 1B and 10 illustrate an AAV capsid comprising a heterologous nucleic acid molecule (e.g., a therapeutic gene) (FIG. 1A); empty, partially-full and full capsids (FIG. 1B); and a AAV capsid composed of 60 copies of three viral proteins (VP1, VP2 and VP3) that give rise to a wide range of theoretical capsid stoichiometries (FIG. 10).

As shown in FIG. 7B, the correlation between the measured MS data and the known SV-AUC data is good.

DETAILED DESCRIPTION

Figure 2:
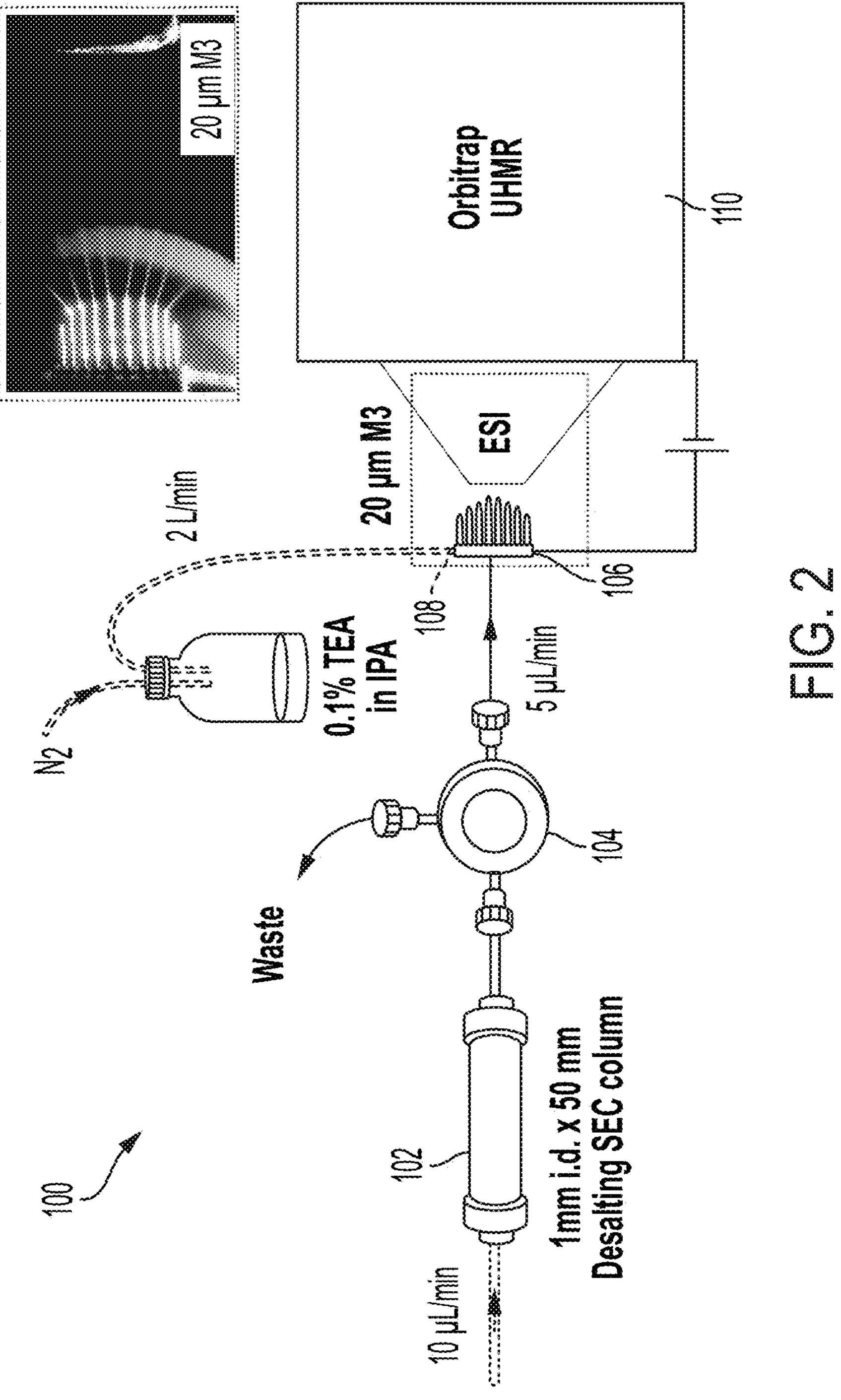
FIG. 2 illustrates an exemplary LC-MS system 100 in accordance with an embodiment of the present disclosure, comprising a liquid chromatography column 102 (e.g. SEC column) coupled to a splitter 104, which is in turn coupled to a microfabricated monolithic multinozzle (M3) electrospray ionization emitter 106, which is coupled to a gas inlet port 108 and a mass spectrometer 110 (e.g., Orbitrap™ UHMR).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "include," "includes," and "including," are meant to be non-limiting and are understood to mean "comprise," "comprises," and "comprising," respectively.

Although any methods and materials similar or equivalent to those described herein can be used in the practice or testing of the present invention, the preferred methods and materials are now described. All patents, applications and non-patent publications mentioned in this specification are incorporated herein by reference in their entireties.

Selected Abbreviations

MS: Mass Spectrometry
rAAV: Recombinant AAV Particle or Capsid
AAV: Adeno-Associated Virus
LC: Liquid Chromatography
SEC: Size Exclusion Chromatography
ESI: Electrospray Ionization
SV-AUC: Sedimentation Velocity Analytical Ultracentrifugation
AEX—Anion Exchange Chromatography

Definitions

"Intact viral capsid components" refer to viral capsids (e.g., empty viral capsids, partially-full viral capsids, and/or full viral capsids) that are intact (i.e., have not been denatured or otherwise broken down or disintegrated into their component parts (e.g., different viral proteins) and retain the structural characteristics of a viral capsid (e.g., the icosahedral conformation of an AAV capsid).

The terms "empty viral capsids" or "empty capsids" refer to capsids not containing a heterologous nucleic acid molecule (e.g., a therapeutic gene), as illustrated in FIG. 1B.

The terms "partially-full viral capsids" or "partially full capsids" refer to capsids containing only a portion of a heterologous nucleic acid molecule (e.g., a therapeutic gene), as illustrated in FIG. 1B.

The terms "full viral capsids" or "full capsids" refer to capsids containing a complete heterologous nucleic acid molecule (e.g., a therapeutic gene), as illustrated in FIG. 1B.

The term "sample," as used herein, refers to a mixture of viral particles (e.g., AAV particles) that comprises at least one viral capsid component (i.e., empty capsids, partially-full capsids, and/or full capsids), that is subjected to manipulation in accordance with the methods of the invention, including, for example, separating and analyzing.

The terms "analysis" or "analyzing," are used interchangeably and refer to any of the various methods of separating, detecting, isolating, purifying and/or characterizing viral particles of interest (e.g., AAV capsids). Examples include, but are not limited to, mass spectrometry, e.g., ESI-MS, liquid chromatography, e.g., size exclusion chromatography, and combinations thereof.

"Contacting," as used herein, includes bringing together at least two substances in solution or solid phase, for example contacting a stationary phase of a chromatography material with a sample, such as a sample comprising viral particles.

"Intact mass analysis" as used herein includes experiments wherein a viral particle is characterized as an intact particle. Intact mass analysis can reduce sample preparation to a minimum.

As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reverse phase liquid chromatography, ion-exchange chromatography, size exclusion chromatography, affinity chromatography, and hydrophobic chromatography.

As used herein, the term "mass spectrometer" refers to a device capable of detecting specific molecular species and accurately measuring their masses. The term can be meant to include any molecular detector into which a viral particle (e.g., AAV capsid) may be eluted for detection and/or characterization. A mass spectrometer consists of three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends on the application. As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray emitter needle containing the solution and a counter electrode. There are three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray ionization source" refers to an electrospray ionization system that can be compatible with a mass spectrometer used for mass analysis of viral particles.

Native MS is a particular approach based on electrospray ionization in which the biological analytes are sprayed from a nondenaturing solvent. It is defined as the process whereby biomolecules, such as large biomolecules, and complexes thereof can be transferred from a three-dimensional, functional existence in a condensed liquid phase to the gas phase via the process of electrospray ionization mass spectrometry (ESI-MS).

The term "nanoelectrospray" or "nanospray" as used herein refers to electrospray ionization at a very low solvent flow rate, typically hundreds of nanoliters per minute of sample solution or lower, often without the use of an external solvent delivery.

As used herein, "mass analyzer" refers to a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, "mass-to-charge ratio" or "m/z" is used to denote the dimensionless quantity formed by dividing the mass of an ion in unified atomic mass units by its charge number (regardless of sign). In general, empty, partially-full and full AAV capsids possess a similar number of charges during native ESI, such that native m/z spectra can be used to directly interpret the fractional composition of AAV capsid components in a sample from differences in the m/z range and relative abundances.

As used herein, the term "quadrupole-Orbitrap hybrid mass spectrometer" refers to a hybrid system made by coupling a quadrupole mass spectrometer to an orbitrap mass analyzer. A tandem in-time experiment using the quadrupole-Orbitrap hybrid mass spectrometer begins with ejection of all ions except those within a selected, narrow m/z range from the quadrupole mass spectrometer. The selected ions can be inserted into orbitrap and fragmented most often by low-energy CID. Fragments within the m/z acceptance range of the trap should remain in the trap, and an MS-MS spectrum can be obtained.

"Adeno-associated virus" or "AAV" is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the Dependovirus genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups.

A "recombinant viral particle" refers to a viral particle including one or more heterologous sequences (e.g., a nucleic acid sequence not viral origin) that may be flanked by at least one viral nucleotide sequence.

A "recombinant AAV particle" refers to a adeno-associated viral particle including one or more heterologous sequences (e.g., nucleic acid sequence not of AAV origin) that may be flanked by at least one, for example, two, AAV inverted terminal repeat sequences (ITRs). Such rAAV particles can be replicated and packaged when present in a host cell that has been infected with a suitable helper virus (or that is expressing suitable helper functions) and that is expressing AAV rep and cap gene products (i.e., AAV Rep and Cap proteins).

A "viral particle" refers to a viral particle composed of at least one viral capsid protein and an encapsulated viral genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral particle is a heterologous nucleotide sequence with respect to the viral particle.

An "inverted terminal repeat" or "ITR" sequence is relatively short sequences found at the termini of viral genomes which are in opposite orientation. An "AAV inverted terminal repeat (ITR)" sequence, is an approximately 145-nucleotide sequence that is present at both termini of a single-stranded AAV genome.

General Description

The present disclosure provides online chromatographic and native mass spectrometry (MS) methods that provide sensitive and rapid quantitative characterization of the viral capsid components (e.g., full capsids, partially-full capsids, and empty capsids) of a sample of viral particles (e.g., AAV particles), and purification methods employing such analytical techniques. Complete characterization of the viral capsid components of viral particle compositions, such as the viral capsid components of a sample of AAV particles, is necessary to ensure product quality and consistency to maintain safety and efficacy of the compositions.

Recombinant viral vector compositions (e.g., AAV vector compositions) can contain varying levels of full, partial, and empty capsids arising from various production, purification and storage conditions. However, high mass heterogeneity arising from variation in viral protein stoichiometries and variation in content of heterologous nucleic acid material, as well as low sample concentrations, makes traditional intact mass spectrometry of such samples challenging. The present methods address these issues by limiting sample dilution (e.g., by low flow rate requirements), by providing fast online desalting (to maintain sample stability), and by providing charge reduction to improve resolution of viral particle species (e.g., AAV capsids).

Methods for Determining Relative Abundance of Intact Viral Capsid Components Aspects of the disclosure are directed to methods for determining the relative abundance of intact viral capsid components in a sample of recombinant viral particles comprising a heterologous nucleic acid molecule.

In some cases, the method comprises: (a) introducing the sample of viral particles into an online native liquid chromatography mass spectrometry (LC-MS) system, wherein the LC-MS system comprises a liquid chromatography column in fluid communication with an electrospray ionization emitter, a mass spectrometer, and a gas inlet port; (b) separating the viral capsid components in the sample of viral particles via the liquid chromatography column; (c) contacting the viral capsid components with a charge reducing agent via the gas inlet port prior to subjecting the viral capsid components to mass spectral analysis; (d) identifying a raw fractional amount of a viral capsid component in the sample via mass spectral analysis; and (e) applying a correction factor to the raw fractional amount of the viral capsid component and identifying a corrected fractional amount of the viral capsid component to thereby determine the relative abundance of each of two or more intact viral capsid components in the sample of viral particles, wherein the correction factor is predetermined by subjecting a reference standard to the online native LC-MS system and identifying a fractional amount of a standard viral capsid component in the reference standard, and comparing the identified fractional amount of the standard viral capsid component against a known fractional amount of the standard viral capsid component, as determined by sedimentation velocity analytical ultracentrifugation (SV-AUC).

In some cases, the method comprises: (a) subjecting the sample of viral particles to online native electrospray ionization mass spectrometry (ESI-MS) to identify a raw fractional amount of a viral capsid component, wherein the sample is subjected to chromatographic separation and a charge reducing agent prior to native ESI-MS; and (b) applying a correction factor to the raw fractional amount of the viral capsid component and identifying a corrected fractional amount of the viral capsid component to thereby determine the relative abundance of the intact viral capsid component in the sample of viral particles, wherein the correction factor is predetermined by subjecting a reference standard to the online native ESI-MS and identifying a fractional amount of a standard viral capsid component in the reference standard, and comparing the identified fractional amount of the standard viral capsid component against a known fractional amount of the standard viral capsid component, as determined by sedimentation velocity analytical ultracentrifugation (SV-AUC).

In various embodiments of the methods, the viral capsid components include empty viral capsids and full viral capsids, and a corrected fractional amount of empty viral capsids and a corrected fractional amount of full viral capsids are identified. In some cases, the viral capsid components further include partially-full viral capsids, and a corrected fractional amount of the partially-full viral capsids is identified. Thus, in some embodiments the methods disclosed herein can be used to identify the relative abundance of empty viral capsids, partially-full viral capsids, and full viral capsids in a sample of recombinant viral particles (e.g., AAV particles).

In the methods disclosed herein, the LC-MS system is exemplified by the schematic illustrated in FIG. 2. In the example shown in FIG. 2, the LC-MS system 100 includes a liquid chromatography column 102 (e.g., a 1 mm internal diameter×50 mm SEC column) into which the sample of viral particles is introduced at, for example, a flow rate of 10 μL/min to separate the viral capsid components of the sample from one another and from any impurities (e.g., salt) that may be present in the sample. The separated components then pass through a splitter 104 and into an electrospray ionization emitter 106 at a flow rate of, for example, 5 μL/min. The ESI emitter 106 is coupled to a gas inlet port 108 through which a modified desolvation gas (e.g., nitrogen modified with a charge reducing agent ("modifier") such as triethylamine in isopropanol) contacts the sample prior to mass spectral analysis in the mass spectrometer 110 (e.g., an Orbitrap™ UHMR mass spectrometer).

In the various methods discussed herein, mass spectral analysis of the sample yields mass spectra showing the relative abundance of the viral capsid components of the sample of viral particles, which are separated by mass based on the content of the heterologous nucleic acid molecule contained in the capsid. As will be appreciated, the mass of the full capsid (which contains the complete heterologous nucleic acid molecule), is greater than the mass of the partially-full capsid (which contains only a part of the heterologous nucleic acid molecule), which is in turn greater than the mass of the empty capsid (which contains none of the heterologous nucleic acid molecule). Given the stoichiometric variation in the viral proteins of the capsids (e.g., FIG. 10), the mass spectrum produced from the mass spectrometric analysis of a sample may contain broad peaks representing each of the viral capsid components in the sample.

Viral Particles

In certain aspects, the viral particle is an AAV particle and the methods disclosed can be used to determine the relative abundance of viral capsid components in a sample of AAV particles. The AAV particles may be recombinant AAV (rAAV) particles. The rAAV particle include an AAV vector encoding a heterologous transgene or heterologous nucleic acid molecule.

In certain aspects, the AAV particles includes an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof. In certain aspects, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some embodiments, the AAV particles are of serotype AAV1, AAV5 or AAV8.

While AAV was the model viral particle for this disclosure, it is contemplated that the disclosed methods can be applied to characterize a variety of viruses, for example, the viral families, subfamilies, and genera. The methods of the present disclosure may find use, for example, in characterizing viral particles to monitor or detect relative abundance of viral capsid components in a composition of viral particles during production, purification or storage of such compositions.

In exemplary embodiments, the viral particle belongs to a viral family selected from the group consisting of Adenoviridae, Parvoviridae, Retroviridae, Baculoviridae, and Herpesviridae.

In certain aspects, the viral particle belongs to a viral genus selected from the group consisting of Atadenovirus, Aviadenovirus, lchtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus, and Rhadinovirus.

In certain aspects, the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend virus, Murine Stem Cell Virus (MSCV) Rous Sarcoma Virus (RSV), human T cell leukemia viruses, Human Immunodeficiency Viruse (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

In some aspects, the viral particle (e.g., AAV particle) contains a heterologous nucleic acid molecule (e.g., a therapeutic gene). In some aspects, the heterologous nucleic acid molecule is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit .beta.-globin promoter and the elongation factor 1-alpha promoter (EF1-alpha) promoter. In some aspects, the promoter comprises a human .beta.-glucuronidase promoter or a cytomegalovirus enhancer linked to a chicken .beta.-actin (CBA) promoter. The promoter can be a constitutive, inducible or repressible promoter. In some aspects, the invention provides a recombinant vector comprising a nucleic acid encoding a heterologous transgene of the present disclosure operably linked to a CBA promoter. In some cases, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further aspect, other native expression control elements, such as enhancer elements, polyadenylation sites or Kozak consensus sequences may also be used to mimic the native expression.

Online Native Liquid Chromatography Mass Spectrometry (LC-MS) System

In some exemplary embodiments, the methods include subjecting a viral particle to liquid chromatography/mass spectrometry (LC/MS). As is known in the art, LC/MS utilizes liquid chromatography for physical separation of ions and mass spectrometry for generation of mass spectral data from the ions. Such mass spectral data may be used to determine, for example, molecular weight or structure, identification of particles by mass, quantity, purity, and so forth. These data may represent properties of the detected ions such as signal strength (e.g., abundance) over time (e.g., retention time), or relative abundance over mass-to-charge ratio. The exemplary LC-MS system illustrated in FIG. 2 can be used to determine relative abundance of viral capsid components in a sample of viral particles. However, modifications to the illustrated exemplary system can also be employed to determine relative abundance of intact viral capsid components.

Non-limiting examples of the liquid chromatography column 102 include reverse phase liquid chromatography, ion-exchange chromatography, size exclusion chromatography, affinity chromatography, hydrophilic-interaction chromatography, and hydrophobic chromatography. Liquid chromatography, including HPLC, can be used to separate components of a sample of viral particles.

In various embodiments, the column temperature can be maintained at a constant temperature throughout the chromatography run. In particular, the column temperature is maintained at ambient room temperature (i.e., about 23-25° C.). In some embodiments, the column is maintained at a temperature in the range of from about 22° C. to about 28° C. In some embodiments, the column is maintained at a temperature in the range of from about 23° C. to about 27° C. In some embodiments, the column is maintained at a temperature in the range of from about 24° C.±1° C. to about 26° C.±1° C. In some cases, the column temperature is maintained in the range of from about 22° C. to about 26° C. In some cases, the column is maintained at a temperature of, or of about, 22° C., 22.5° C., 23° C., 23.5° C., 24° C., 24.5° C., 25° C., 25.5° C., 26° C., 26.5° C., 27° C., 27.5° C., or 28° C. In some embodiments, the temperature is maintained using a commercial column heater. In some embodiments, the temperature is ambient room temperature (without use of a column heater).

In some embodiments, LC analysis includes a size exclusion chromatography (SEC) column in fluid communication with a native mass spectrometry system. In various embodiments, the LC analysis can be performed as known in the art, but it is noteworthy that use of an anion-exchange column may lead to reduced resolution between partially-full and full capsids. The columns are suitable for use with viral particles. In one embodiment, the SEC column is a Waters BEH® SEC column (1×50 mm).

The column, such as a SEC, is in fluid communication with the mass spectrometer via an analytical flow splitter 104 that can adjust the flow rate to the mass spectrometer.

In some embodiments, the mobile phase is an aqueous mobile phase. In some embodiments, the mobile phase is an aqueous salt buffer containing ammonium acetate. In some embodiments, an isocratic elution (e.g., constant buffer composition maintained throughout the run) is employed. In exemplary embodiments, the mobile phase used to elute the protein is a mobile phase that is compatible with a mass spectrometer. Gradients of the buffer(s) can be used, for example, if two buffers are used, the concentration or percentage of the first buffer can decrease while the concentration or percentage of the second buffer increases over the course of the chromatography run. For example, the percentage of the first buffer can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% over the course of the chromatography run. As another example, the percentage of the second buffer can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% over the course of the same run. In certain aspects, the proportion of mobile phase A in the chromatography increases over time. Optionally, the concentration or percentage of the first and second buffer can return to their starting values at the end of the chromatography run. The percentages can change gradually as a linear gradient or in a non-linear (e.g., stepwise) fashion. For example, the gradient can be multiphasic, for example, biphasic, triphasic, etc.

In some exemplary embodiments, the mobile phase can have a flow rate through the liquid chromatography column of about 0.1 μL/min to about 100 μL/min. In some cases, the flow rate is about 0.5 μL/min, about 1 μL/min, about 1.5 μL/min, about 2 μL/min, about 2.5 μL/min, about 3 μL/min, about 3.5 μL/min, about 4 μL/min, about 4.5 μL/min, about 5 μL/min, about 5.5 μL/min, about 6 μL/min, about 6.5

μL/min, about 7 μL/min, about 7.5 μL/min, about 8 μL/min, about 8.5 μL/min, about 9 μL/min, about 9.5 μL/min, about 10 μL/min, about 10.5 μL/min, about 11 μL/min, about 11.5 μL/min, about 12 μL/min, about 12.5 μL/min, about 13 μL/min, about 13.5 μL/min, about 14 μL/min, about 14.5 μL/min, about 15 μL/min, about 15.5 μL/min, about 16 μL/min, about 16.5 μL/min, about 17 μL/min, about 17.5 μL/min, about 18 μL/min, about 18.5 μL/min, about 19 μL/min, about 19.5 μL/min, about 20 μL/min, about 25 μL/min, about 30 μL/min, about 35 μL/min, about 40 μL/min, about 45 μL/min, about 50 μL/min, about 75 μL/min, or about 100 μL/min. In some cases, the flow rate is 10 μL/min.

In some aspects, mass spectrometry (e.g., used in LC/MS as described herein) may refer to electrospray ionization mass spectrometry (ESI-MS). ESI-MS is known in the art as a technique that uses electrical energy to analyze ions derived from a solution using mass spectrometry. Ionic species, including neutral species that are ionized in solution or in gaseous phase, are transferred from a solution to a gaseous phase by dispersal in an aerosol of charged droplets. Subsequently, solvent evaporation is conducted to reduce the size of the charged droplets. Then, sample ion is ejected from the charge droplets as the solution passing through a small capillary with a voltage relative to ground. For example, the wall of the surrounding ESI chamber is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one aspect, the eluted sample is deposited directly from the capillary into an electrospray nozzle, for example, the capillary functions as the sample loader. In another aspect, the capillary itself functions as both the extraction device and the electrospray nozzle.

In some exemplary embodiments, the electrospray ionization emitter 108 comprises multiple emitter nozzles, such as at least two, at least three, at least four, at least five, at least six, at least seven, at least eight emitter nozzles, such as two, three, four, five, six, seven or eight emitter nozzles. In some exemplary embodiments, the electrospray ionization emitter 108 is a M3 emitter from Newomics (Berkeley, CA) which includes 8 emitter nozzles.

In some exemplary embodiments, other ionization modes are used for example, turbospray ionization mass spectrometry, nanospray ionization mass spectrometry, thermospray ionization mass spectrometry, sonic spray ionization mass spectrometry, SELDI-MS and MALDI-MS. In general, an advantage of these methods (like ESI-MS) is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem can be addressed by presenting the analyte in low salt and/or by the use of a volatile salt. In the case of MALDI, the analyte should be in a solvent compatible with spotting on the target and with the ionization matrix employed.

In some exemplary embodiments, a modified desolvation gas (e.g., nitrogen) can be introduced via the gas inlet port 108 to contact the sample prior to mass spectral analysis. In various embodiments, the modifier comprises at least one organic solvent and a base. Non-limiting examples of organic solvents include acetonitrile, propanol, isopropanol, water and methanol. Non-limiting examples of base include ammonia, diethylamine, triethylamine, N,N-diisopropylehtylamine (DIPEA), and piperidine. In some exemplary embodiments, the modifier is triethylamine in isopropanol.

In some exemplary embodiments, the electrospray ionization source provides an electrospray with a solvent flow rate of from about 1 μL/min to about 20 μL/min. In various embodiments, the flow rate into the ESI emitter is about 1 μL/min, about 2 μL/min, about 3 μL/min, about 4 μL/min, about 5 μL/min, about 6 μL/min, about 7 μL/min, about 8 μL/min, about 9 μL/min, about 10 μL/min, about 11 μL/min, about 12 μL/min, about 13 μL/min, about 14 μL/min, about 15 μL/min, about 16 μL/min, about 17 μL/min, about 18 μL/min, about 19 μL/min, or about 20 μL/min.

The native mass spectrometer can be a native ESI mass spectrometry system. In some exemplary embodiments, the mass spectrometer 110 can be a quadrupole-Orbitrap hybrid mass spectrometer. The quadrupole-Orbitrap hybrid mass spectrometer can be Q Exactive™ Focus Hybrid Quadrupole-Orbitrap™ Mass Spectrometer, Q Exactive™ Plus Hybrid Quadrupole-Orbitrap™ Mass Spectrometer, Q Exactive™ BioPharma Platform, Q Exactive™ UHMR Hybrid Quadrupole-Orbitrap™ Mass Spectrometer, Q Exactive™ HF Hybrid Quadrupole-Orbitrap™ Mass Spectrometer, Q Exactive™ HF-X Hybrid Quadrupole-Orbitrap™ Mass Spectrometer, and Q Exactive™ Hybrid Quadrupole-Orbitrap™ Mass Spectrometer. In some exemplary embodiments, the mass spectrometry system is a Thermo Exactive EMR mass spectrometer. The mass spectrometry system can also contain an ultraviolet light detector.

A variety of mass analyzers suitable for LC/MS are known in the art, including without limitation time-of-flight (TOF) analyzers, quadrupole mass filters, quadrupole TOF (QTOF), and ion traps (e.g., a Fourier transform-based mass spectrometer or an Orbitrap). In Orbitrap, a barrel-like outer electrode at ground potential and a spindle-like central electrode are used to trap ions in trajectories rotating elliptically around the central electrode with oscillations along the central axis, confined by the balance of centrifugal and electrostatic forces. The use of such instruments employs a Fourier transform operation to convert a time domain signal (e.g., frequency) from detection of image current into a high resolution mass measurement.

Methods of Purifying Compositions of Viral Particles

Methods of purifying a composition of viral particles are also provided. In some aspects, the methods comprise a chromatographic enrichment step (e.g., an anion-exchange enrichment step) and a determination of a relative abundance of intact viral capsid components in a sample of the composition, wherein the determination of relative abundance of intact viral capsid components comprises any one of the methods discussed above.

In some embodiments, the determination of a relative abundance of intact viral capsid components in the sample of the composition is performed before the chromatographic enrichment step (e.g., AEX chromatography). In some embodiments, the determination of a relative abundance of intact viral capsid components is performed after the chromatographic enrichment step (e.g., AEX chromatography). In some embodiments, the determination of a relative abundance of intact viral capsid components is performed before the chromatographic enrichment step (e.g., AEX chromatography) and after the chromatographic enrichment step (e.g., AEX chromatography). In some cases, the chromatographic enrichment step is an anion-exchange enrichment step performed using an anion-exchange chromatography column.

Methods of Monitoring Stability of Viral Particles

Methods of monitoring stability of a sample of viral particles over a period of time are also provided. In some aspects, the methods comprise a chromatographic enrichment step (e.g., an anion-exchange enrichment step) and a determination of a relative abundance of intact viral capsid components in a sample of viral particles at an initial time point (t0) and again at one or more time points following the initial time point (e.g., days, weeks, or months later)

A change in the relative abundance of the intact viral capsid components at the one or more time points compared to the relative abundance at the initial time point is indicative of the stability of the sample of viral particles during the period of time. For example, a reduction in the relative abundance of full viral capsids over a period of time under specified conditions provides an indication of the relative stability of the sample of viral particles under such specified conditions during the period of evaluation (i.e., from t0 to the later time point at which the relative abundance of viral capsid components is again determined). In some cases, the sample of viral particles is stored under specified conditions during the period of time. In some cases, the specified conditions include humidity conditions (e.g., 60% or 75% relative humidity) and/or temperature conditions (e.g., 0° C., 2-5° C., 15° C., 25° C., 45° C.). In some cases, the specified conditions include (or further include) agitation conditions (e.g., agitation on an orbital shaker for a period of from 30-90 minutes) and/or one or more freeze/thaw cycles. These conditions may be chosen to monitor stability of the viral capsid samples under real-world or accelerated conditions to monitor or characterize the stability of the samples.

In some embodiments, the determination of a relative abundance of intact viral capsid components in the sample of viral particles is performed before the chromatographic enrichment step (e.g., AEX chromatography). In some embodiments, the determination of a relative abundance of intact viral capsid components is performed after the chromatographic enrichment step (e.g., AEX chromatography). In some embodiments, the determination of a relative abundance of intact viral capsid components is performed before the chromatographic enrichment step (e.g., AEX chromatography) and after the chromatographic enrichment step (e.g., AEX chromatography). In some cases, the chromatographic enrichment step is an anion-exchange enrichment step performed using an anion-exchange chromatography column.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Determination of Relative Abundance of Intact Viral Capsid Components in Samples of AAV Particles Aliquots of AAV stock solutions or in-process samples were stored at −80° C. and diluted in water at 1:2 to 1:10 immediately prior to analysis. Online native desalting SEC-MS was performed using a Waters BEH200 SEC guard column (1×50 mm) with an isocratic elution of 150 mM ammonium acetate at 10 μL/min on a native LC-MS platform adapted for low flow conditions (see FIG. 2). The resulting AAV eluent was then subjected to frontend charge reduction using 0.01% (v/v) TEA in IPA-modified desolvation gas (2 L/min, nitrogen) followed by native MS analysis using an Orbitrap Q-Exactive UHMR instrument optimized for transmission of high mass ions (see FIG. 2).

Figure 3:
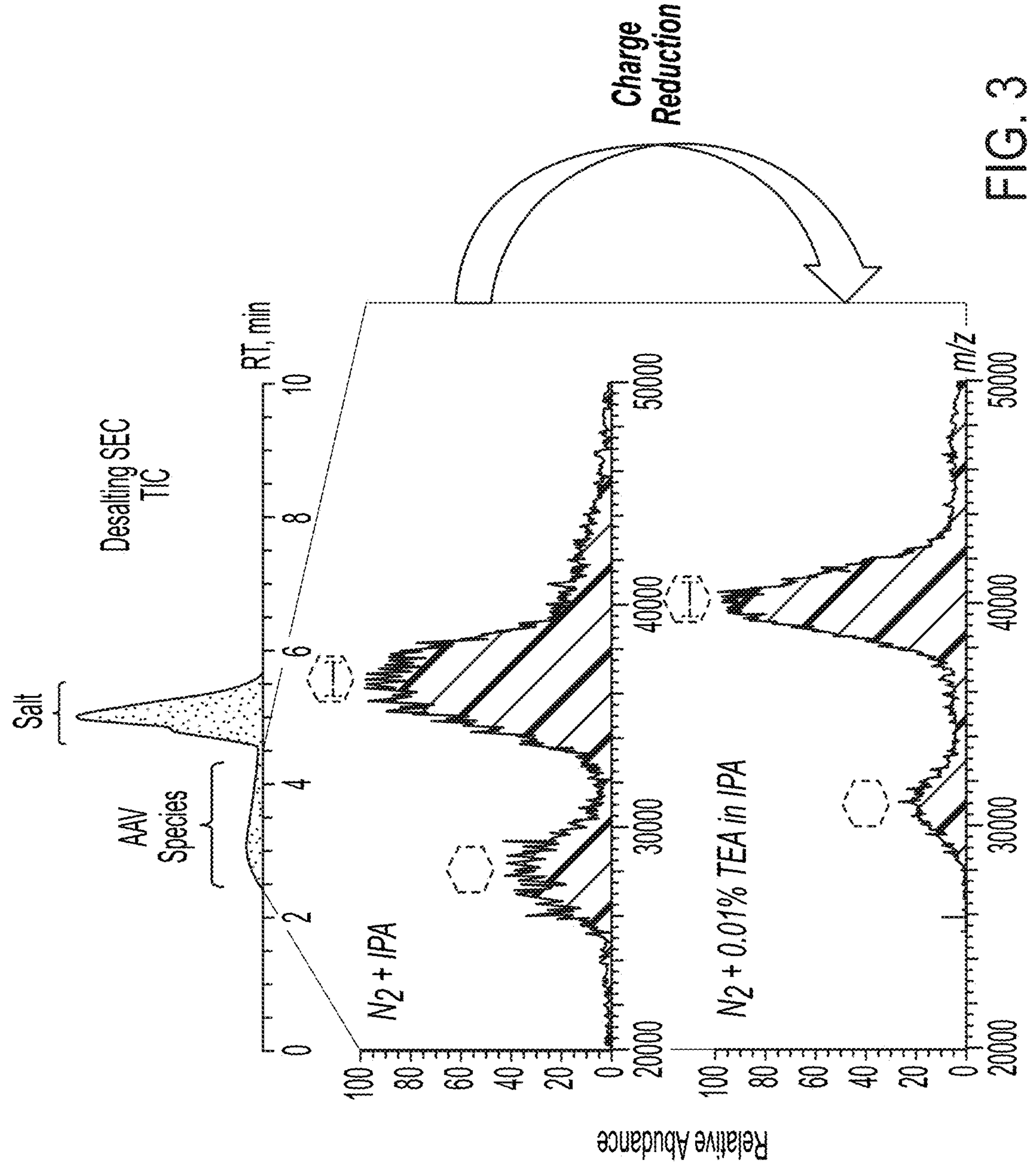
FIG. 3 shows a chromatogram illustrating the separation of AAV capsid components from salt via the liquid chromatography column of FIG. 2, and mass spectra showing the relative abundance of empty viral capsids and full viral capsids. The mass spectra illustrate a difference obtained with (bottom) and without (top) application of a charge reducing agent (e.g., 0.01% triethylamine in isopropanol) to an AAV capsid containing sample prior to mass spectral analysis. Charge reduction improved resolution of the AAV capsid components.
Figures 4A, 4B:
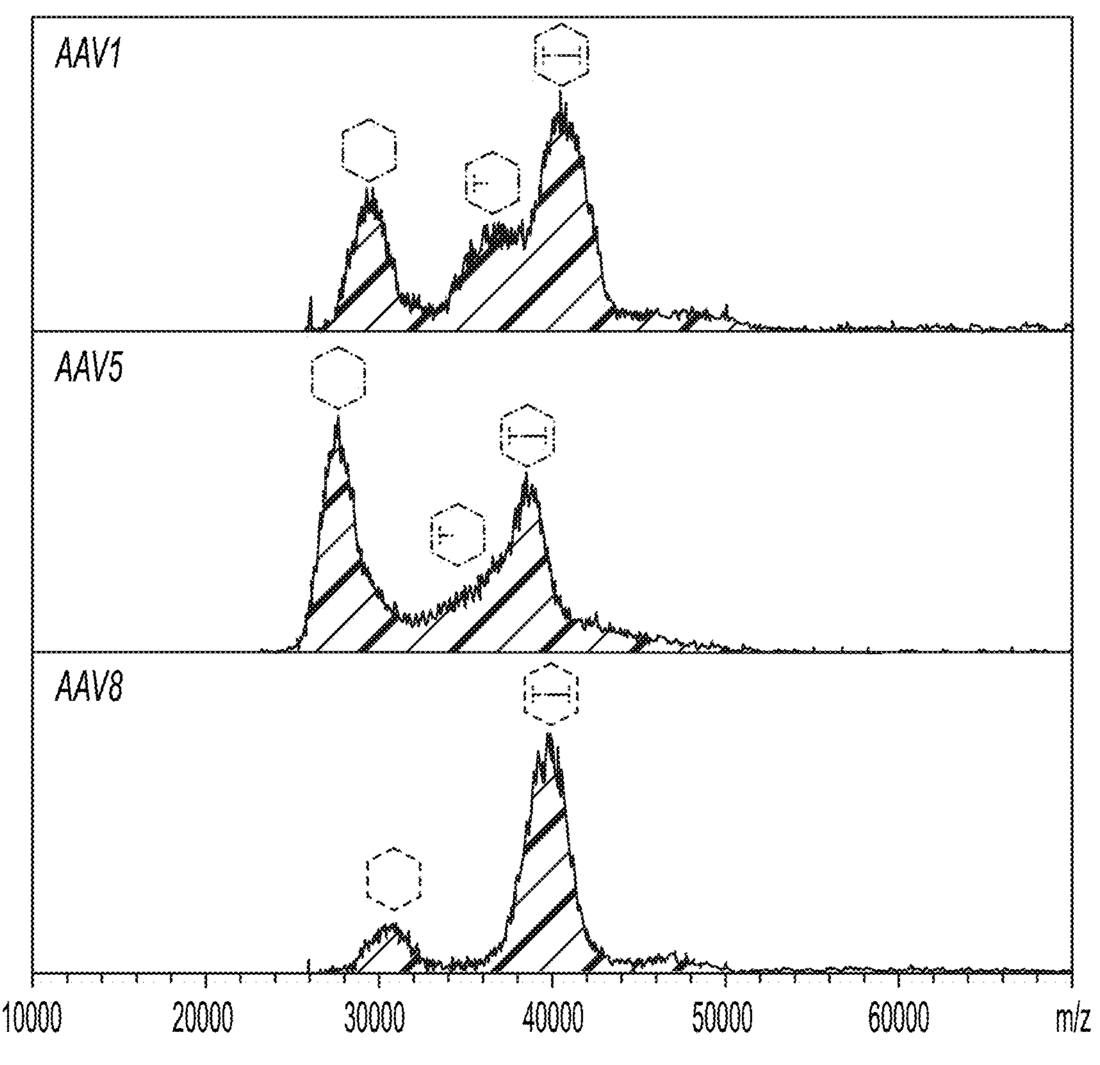
FIGS. 4A and 4B show mass spectra (FIG. 4A) of various AAV serotypes (AAV1, AAV5, and AAV8) and corresponding SV-AUC data for the same AAV serotypes (FIG. 4B). The mass spectra show that the methods of the present disclosure produce results consistent with SV-AUC data across various AAV serotypes.
Figure 5A:
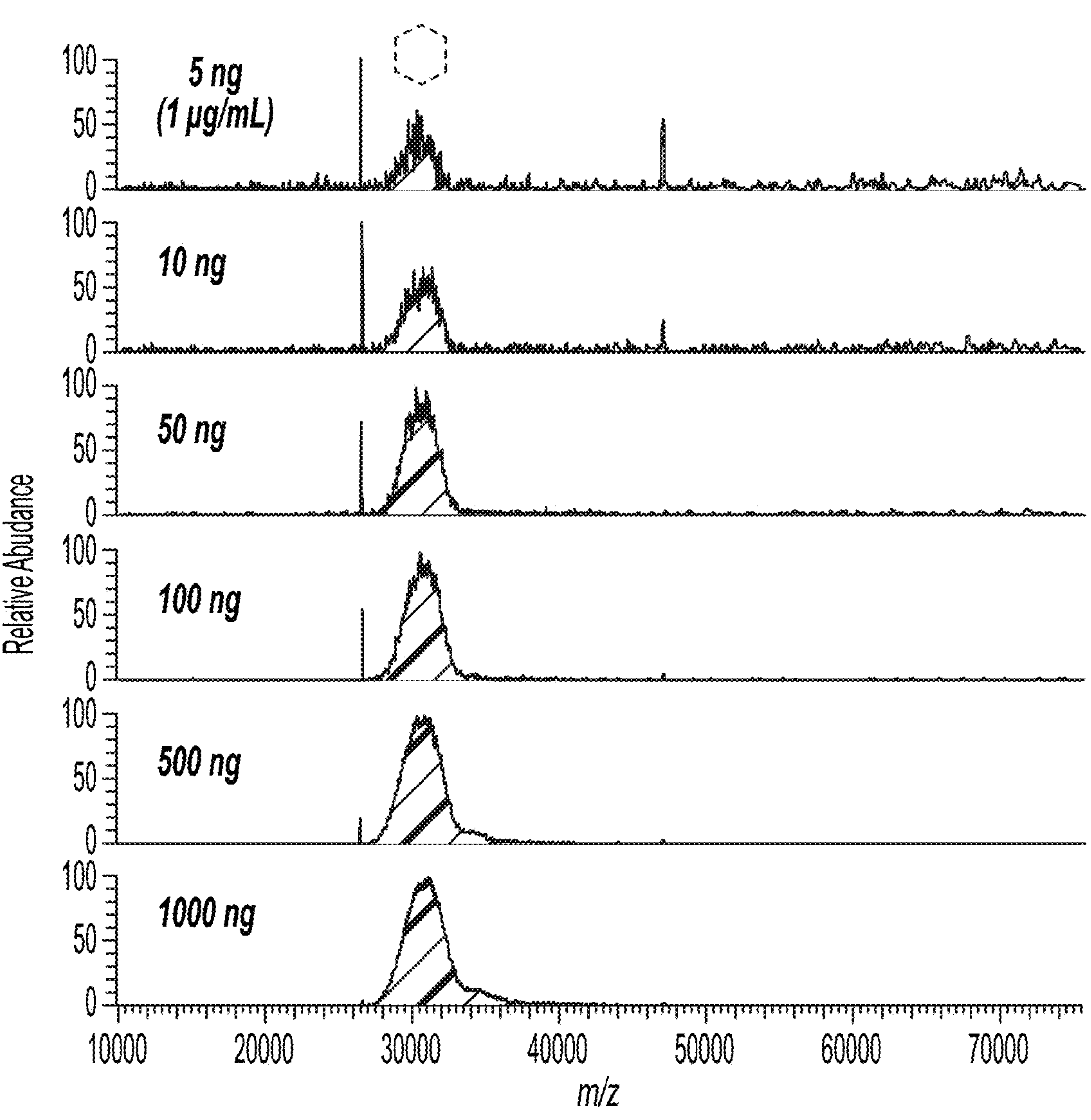
FIGS. 5A and 5B show mass spectra produced from injecting varying quantities of empty capsid AAV material into the LC-MS system of the present disclosure (FIG. 5A) and a correlation between mass spectral response and injection quantity (FIG. 5B). These results demonstrate that the methods of the present disclosure are highly sensitive to detection of viral capsid material (e.g., AAV capsids), which make the methods well-suited to in-process sample monitoring.
Figure 5B:
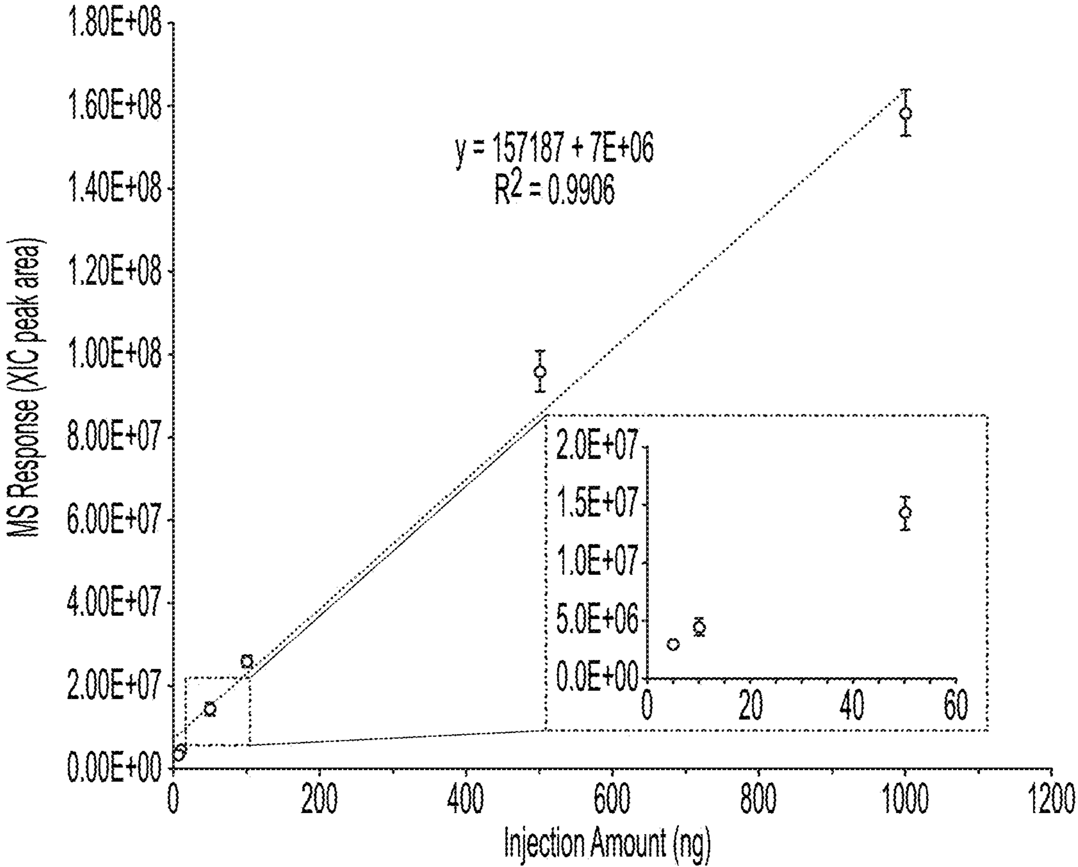
Figure 6:
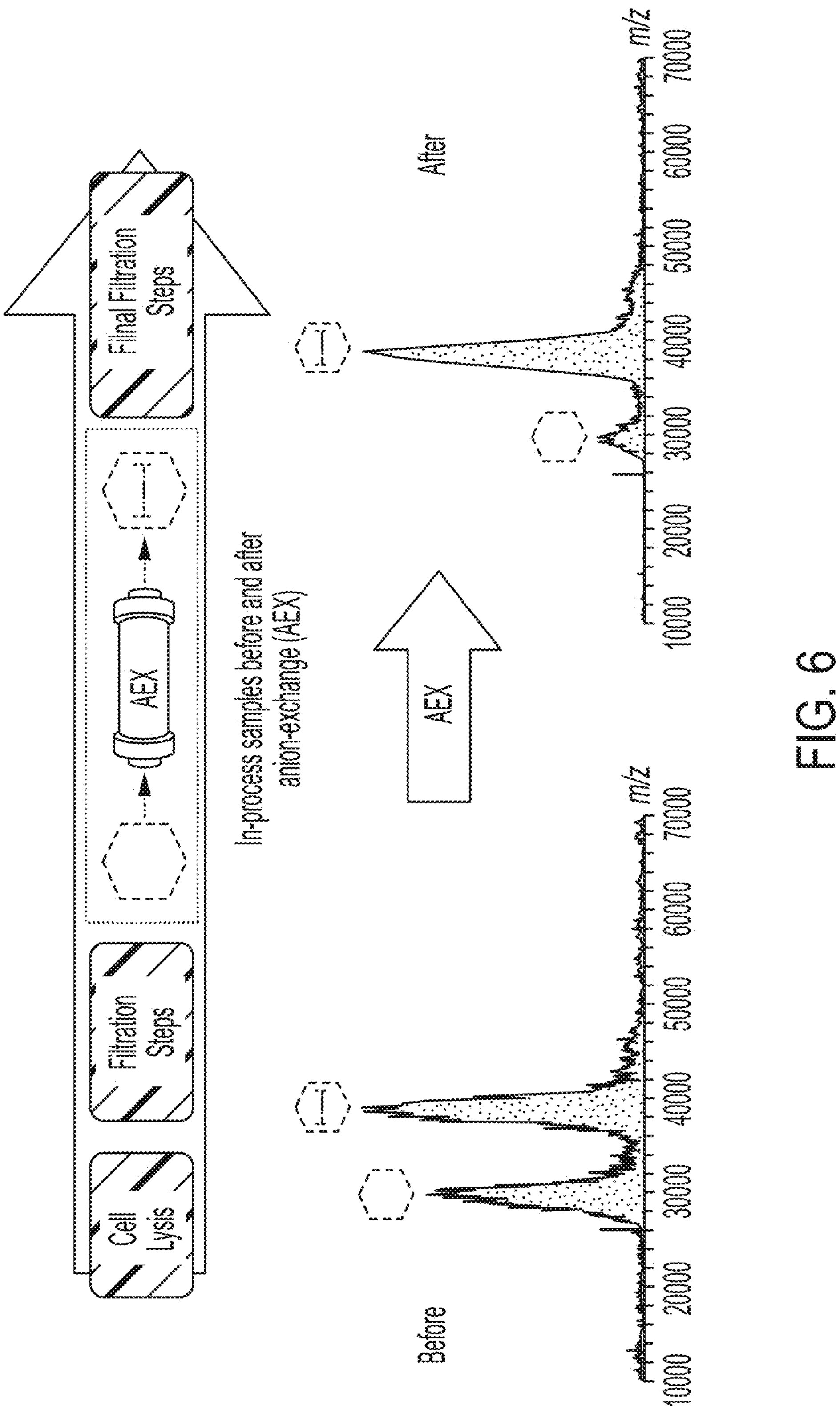
FIG. 6 illustrates an exemplary purification process for viral capsids, which includes an anion-exchange (AEX) column for enrichment of full viral capsids relative to empty viral capsids, and shows mass spectra corresponding to measurements taken before AEX enrichment and after AEX enrichment.
Figure 7A:
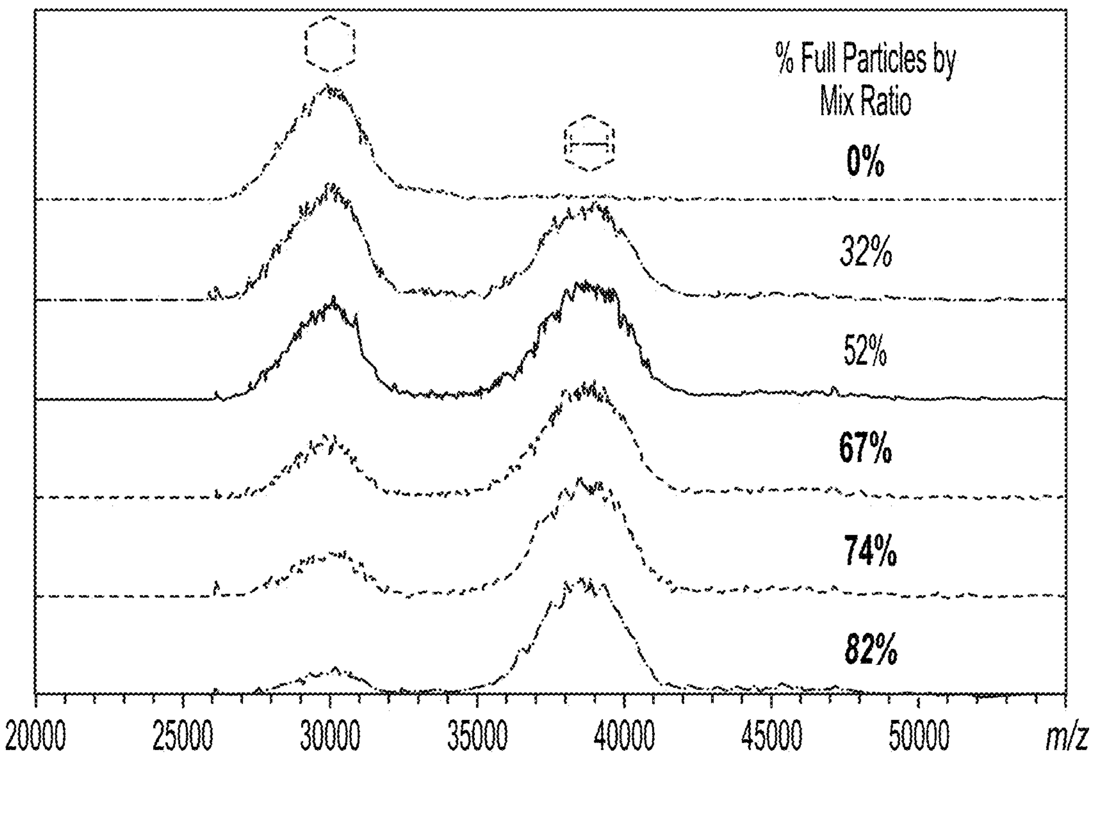
FIGS. 7A and 7B show mass spectra produced from introduction of varying ratios of emply:full AAV capsids into the LC-MS system of the present disclosure (FIG. 7A) and a correlation between known SV-AUC data and the measured percentages of capsid components obtained from the mass spectra (FIG. 7B).
Figure 7B:
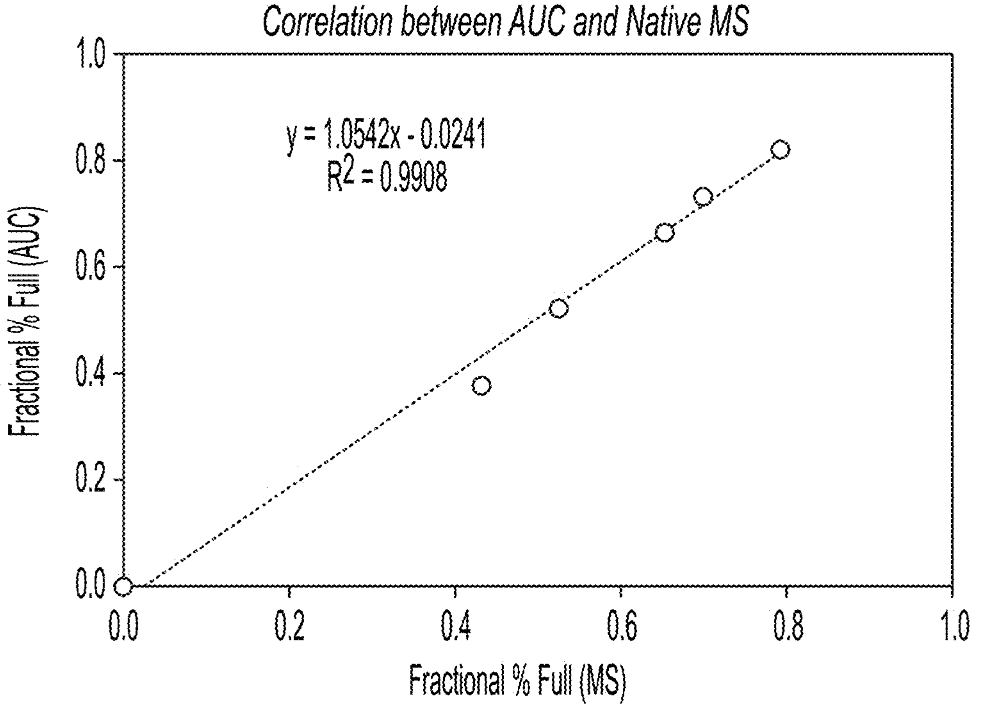
Figure 8:
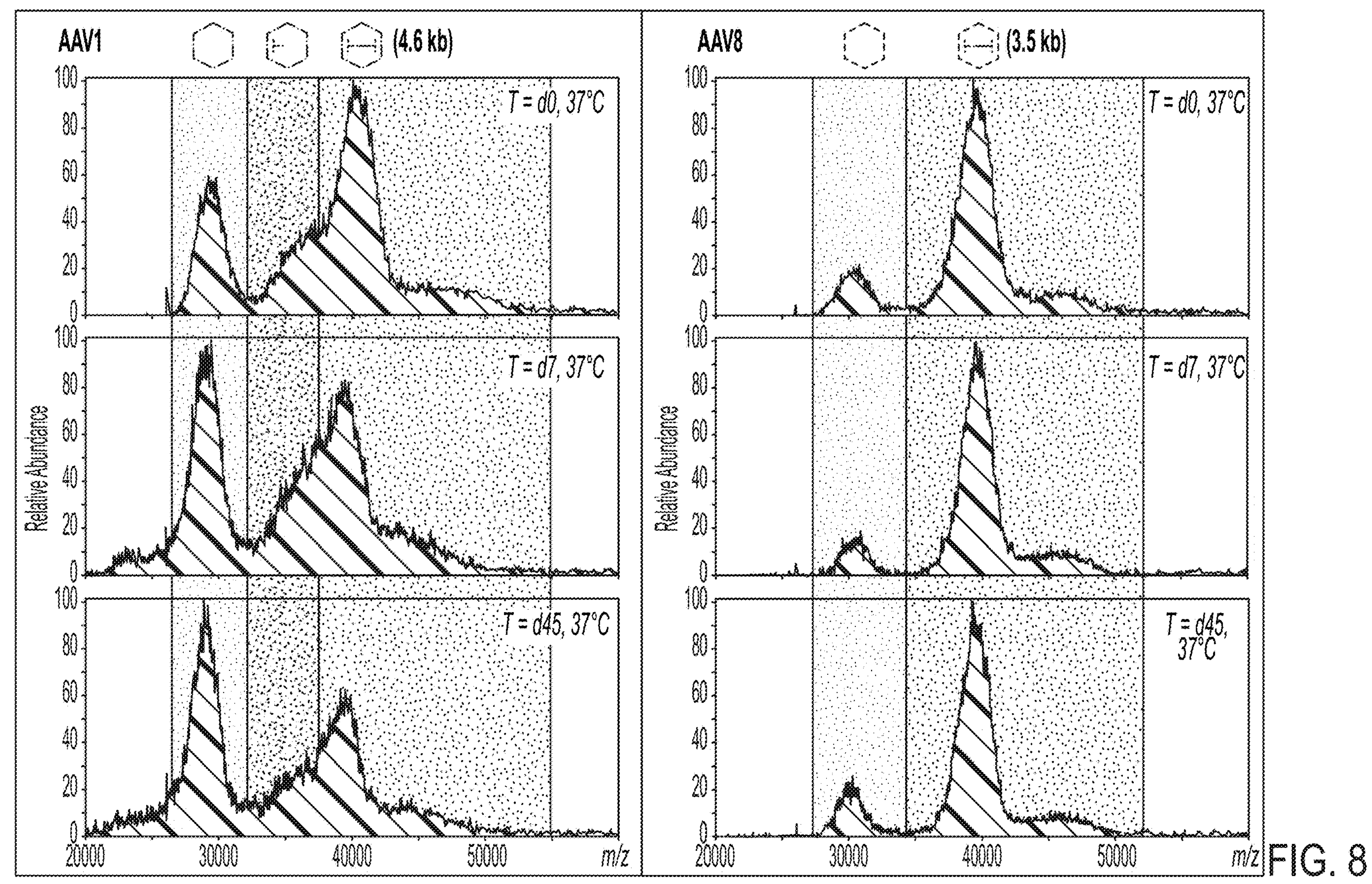
FIG. 8 illustrates exemplary results generated by employing the assay techniques of the present disclosure, whereby changes in capsid stability are monitored following thermal stress.

Charge detection mass spectrometry (CD-MS) studies revealed that empty, partial, and full AAV capsids possess a similar number of charges during native ESI. Thus, native m/z spectra can be used to directly interpret the fractional composition of AAV capsid particles from differences in their m/z range (i.e., m/z∝mass, when z is constant) and relative abundances. In the present methods, native AAV analysis was improved by using an integrated desalting SEC-MS platform to achieve online buffer exchange and total analysis times of 10 min/sample (see FIG. 3). In addition, charge reduction via modification of the desolvation gas enhanced spectral resolution of AAV capsid particles for improved quantitation (see FIG. 3). The methods were performed using low flow conditions (10 μl/min) to limit sample dilution and to facilitate sensitive detection of AAV capsid material with titers as low as 6E+10 capsids/mL (see FIG. 5A). The methods proved amenable to monitoring in-process samples collected before and after AEX-enrichment of the full capsid material (see FIG. 6). The methods discussed above were used to monitor the relative abundance of viral capsid components (AAV1 and AAV8) in samples stored at 37° C. over a period of 45 days, as shown in FIG. 8

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for determining relative abundance of intact viral capsid components in a sample of recombinant viral particles comprising a heterologous nucleic acid molecule, comprising:

(a) introducing the sample of viral particles into an online native liquid chromatography mass spectrometry (LC-MS) system, wherein the LC-MS system comprises a liquid chromatography column in fluid communication with an electrospray ionization emitter, a mass spectrometer, and a gas inlet port;

(b) separating the intact viral capsid components in the sample of viral particles via the liquid chromatography column, wherein a mobile phase flow rate through the liquid chromatography column is from 1 μL/min to 20 μL/min;

(c) contacting the intact viral capsid components with a charge reducing agent via the gas inlet port prior to subjecting the intact viral capsid components to mass spectral analysis; and (d) identifying a raw fractional amount of an intact viral capsid component in the sample via mass spectral analysis to determine the relative abundance of each of two or more intact viral capsid components in the sample of viral particles.

2. The method of claim 1, wherein sample of viral particles comprises adeno-associated virus (AAV) particles.

3. The method of claim 2, wherein the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

4. The method of claim 1, wherein the intact viral capsid components comprise (a) empty viral capsids and full viral capsids, or (b) empty viral capsids, full viral capsids and partially-full viral capsids.

5. The method of claim 1, wherein the liquid chromatography column is a size-exclusion chromatography (SEC) column.

6. The method of claim 1, wherein the charge reducing agent is isopropanol or triethylamine, and/or wherein the viral capsid components are contacted with the charge reducing agent in nitrogen gas.

7. The method of claim 1, wherein the electrospray ionization emitter includes eight nozzles, and/or wherein the mass spectrometer is a charge detection mass spectrometer.

8. The method of claim 1, wherein the sample comprises:

(a) ≤1000 ng of viral capsid components;

(b) ≤500 ng of viral capsid components;

(c) ≤100 ng of viral capsid components;

(d) ≤50 ng of viral capsid components;

(e) ≤10 ng of viral capsid components; or (f) about 5 ng of viral capsid components.

9. The method of claim 1, wherein a concentration of the intact viral capsid components in the sample is:

(a) from 1 μg/mL to 200 μg/mL;

(b) less than 100 μg/mL;

(c) less than 50 μg/mL;

(d) less than 10 μg/mL;

(e) less than 5 μg/mL; or (f) about 1 μg/mL.

10. A method of purifying a composition of viral particles, wherein the method comprises an anion-exchange enrichment step and a determination of a relative abundance of intact viral capsid components in a sample of the composition, wherein the determination of relative abundance of intact viral capsid components comprises the method of claim 1.

11. The method of claim 10, wherein the determination of a relative abundance of intact viral capsid components:

(a) is performed before the anion-exchange enrichment step;

(b) is performed after the anion-exchange enrichment step; or (c) is performed before the anion-exchange enrichment step and after the anion-exchange enrichment step.

12. The method of claim 11, wherein the anion-exchange enrichment step is performed using an anion-exchange chromatography column.

13. A method of monitoring stability of a sample of viral particles over a period of time, wherein the method comprises an anion-exchange enrichment step and a determination of a relative abundance of intact viral capsid components in the sample of viral particles, wherein the determination of relative abundance of intact viral capsid components comprises the method of claim 1, and wherein the relative abundance of intact viral capsid components is determined at an initial time point and again determined at one or more time points following the initial time point.

14. The method of claim 13, wherein a change in the relative abundance of the intact viral capsid components at the one or more time points compared to the relative abundance at the initial time point is indicative of the stability of the sample of viral particles during the period of time.

15. The method of claim 13, wherein the sample of viral particles is stored under specified conditions during the period of time, and wherein the specified conditions include humidity conditions and/or temperature conditions and/or agitation conditions and/or one or more freeze/thaw cycles.

16. A method for determining relative abundance of intact viral capsid components in a sample of recombinant viral particles comprising a heterologous nucleic acid molecule, comprising:

(a) subjecting the sample of viral particles to online native electrospray ionization mass spectrometry (ESI-MS) to identify a raw fractional amount of an intact viral capsid component, wherein the sample is subjected to chromatographic separation and a charge reducing agent prior to the online native ESI-MS, wherein the chromatographic separation comprises a mobile phase flow rate of from 1 μL/min to 20 μL/min; and (b) determining the relative abundance of the intact viral capsid component in the sample of viral particles.

17. The method of claim 16, wherein the viral capsid components include (a) empty viral capsids and full viral capsids, or (b) empty viral capsids, full viral capsids and partially-full viral capsids.

18. The method of claim 16, wherein the sample of viral particles comprises adeno-associated virus (AAV) particles selected from the group consisting of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, and AAV-PHP.S.

19. The method of claim 16, wherein the chromatographic separation is performed using a size-exclusion chromatography (SEC) column.

20. The method of claim 16, wherein the charge reducing agent is isopropanol or triethylamine.

* * * * *